United States Patent
Hargett et al.

(10) Patent No.: US 6,743,324 B2
(45) Date of Patent: Jun. 1, 2004

(54) METHOD FOR MANUFACTURING SHAPED COMPONENTS FROM WEB MATERIALS

(75) Inventors: Mark Mason Hargett, Cincinnati, OH (US); Michael Gary Nease, Fairfield, OH (US); Michael Patrick Hayden, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 225 days.

(21) Appl. No.: 09/953,770

(22) Filed: Sep. 17, 2001

(65) Prior Publication Data

US 2003/0051802 A1 Mar. 20, 2003

(51) Int. Cl.[7] ............................................. B32B 31/00
(52) U.S. Cl. ...................... 156/259; 156/260; 156/264; 156/265; 156/271; 156/301; 156/302; 156/512; 156/519
(58) Field of Search ................................ 156/302, 259, 156/260, 264, 265, 271, 512, 519, 516

(56) References Cited

U.S. PATENT DOCUMENTS

| | | | |
|---|---|---|---|
| 5,580,411 A | 12/1996 | Nease et al. | 156/260 |
| 5,705,013 A | 1/1998 | Nease et al. | 156/260 |
| 5,985,081 A | 11/1999 | Reynolds | 156/271 |
| 6,074,333 A | 6/2000 | Rajala et al. | 493/346 |
| 6,171,432 B1 | 1/2001 | Brisebois et al. | 156/260 |
| 6,227,541 B1 | 5/2001 | Couillard et al. | 271/307 |
| 6,235,142 B1 * | 5/2001 | Koschitzky | 156/260 |

FOREIGN PATENT DOCUMENTS

WO    WO 00/33681    6/2000

* cited by examiner

*Primary Examiner*—Linda L. Gray
(74) *Attorney, Agent, or Firm*—Michael P. Hayden

(57) ABSTRACT

A method for manufacturing shaped components for absorbent articles from web materials including the following steps. A first web of material is provided in a machine direction. The first web is cut into at least two shaped strips having alternating nested projecting portions defined by at least one shaping cut having a pattern extending in the machine direction and alternately extending in the cross machine direction to alternate distal points located between longitudinal side edges of the first web. At least a first and a second of the shaped strips are separated. A second web of material is provided in the machine direction. At least the first shaped strip is joined to the second web. The second web is repositioned in the cross machine direction a predetermined distance. At least the second shaped strip is joined to the second web. The resultant composite web is cut into separate shaped components.

18 Claims, 12 Drawing Sheets

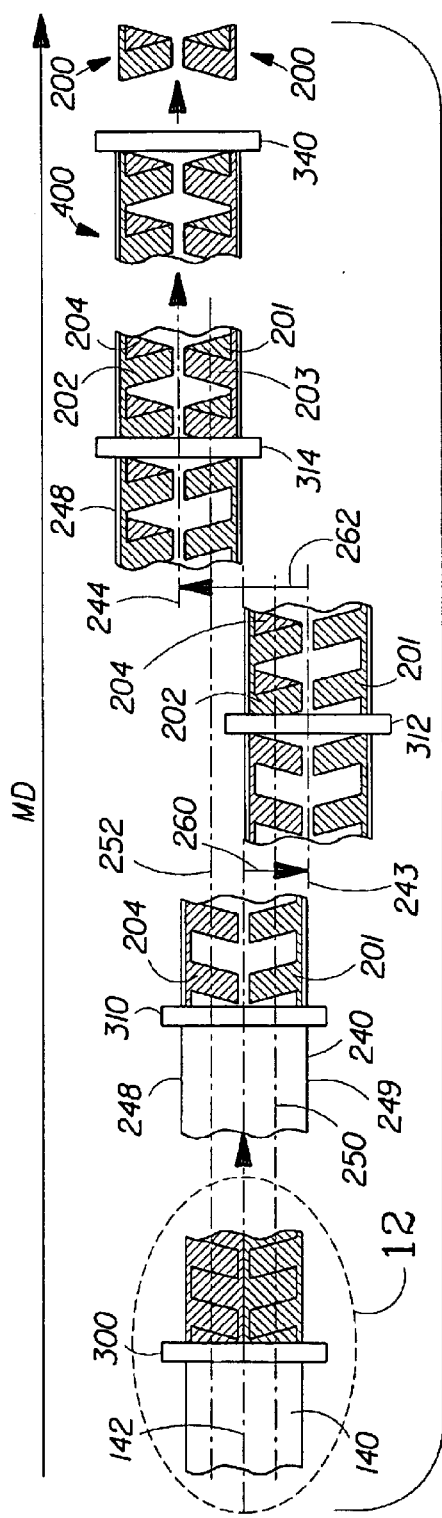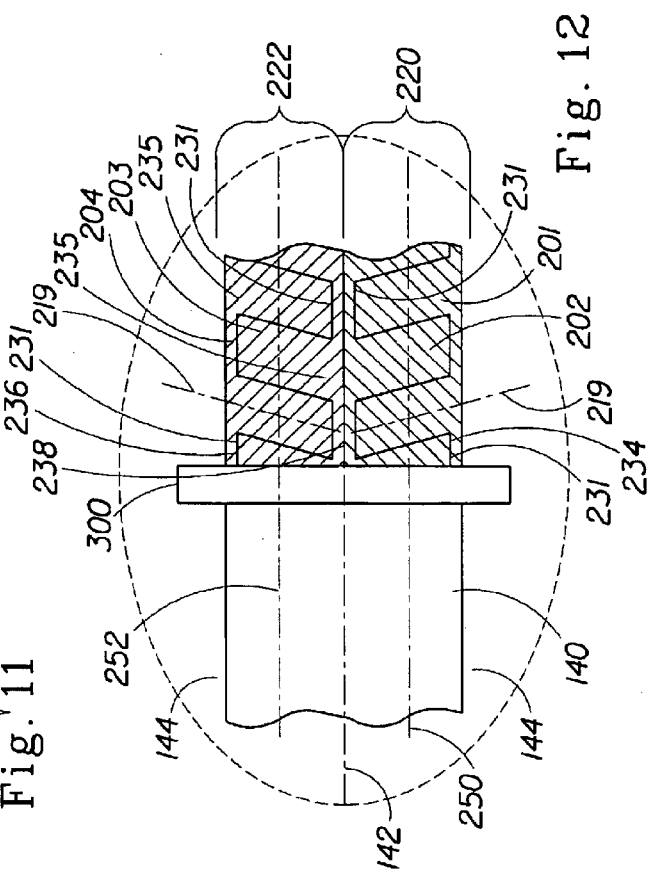
Fig. 11
Fig. 12

METHOD FOR MANUFACTURING SHAPED COMPONENTS FROM WEB MATERIALS

FIELD OF THE INVENTION

This invention relates to a method for manufacturing shaped components and, more particularly, to a method for manufacturing shaped components from web materials. Such shaped components may be used in the construction of absorbent articles, as well as for other articles.

BACKGROUND OF THE INVENTION

Disposable absorbent articles such as diapers, training pants, incontinence garments, feminine hygiene garments and the like often include product features such as side panels that provide a variety of functional benefits. An overriding consideration in the manufacture of a disposable absorbent article is the cost of manufacturing the article, including the materials cost. The present invention provides methods for manufacturing shaped components with little or no waste of the shaped material. Thus, the product features constructed of the shaped components made by the process of the present invention may be provided at a relatively lower cost than many of the features that are currently manufactured using techniques in which material is wasted.

Another important element of the manufacturing cost is related to the losses in efficiency, scrap, and quality due to the difficulty of handling and processing many of the materials having desirable properties in the finished product. For example, many useful elastomeric materials have properties such as a low modulus of elasticity, a high coefficient of friction, a low breaking strength, and the like, which make their handling and processing difficult. The present invention provides methods for manufacturing shaped components in which the shaped materials remain under good control throughout the process. Thus, shaped elastomeric components made by the process of the present invention may be provided at a relatively lower cost than many of the components made using less robust processes. Accordingly, the method of the present invention may reduce the overall cost of the absorbent article.

SUMMARY OF THE INVENTION

The present invention provides a method for manufacturing shaped components from web materials. Such shaped components may be used in the construction of product features such as side panels, shaped ears, and the like, for absorbent articles, as well as for other articles.

In one preferred embodiment, the present invention provides a method including the following steps for manufacturing shaped components. A first web of material is provided in a machine direction. The first web is cut into at least one pair of shaped strips having alternating nested projecting portions defined by at least one shaping cut having a pattern extending in the machine direction and alternately extending in the cross machine direction to alternate distal points located between longitudinal side edges of the first web. At least a first and a second of the shaped strips are separated. A second web of material is provided in the machine direction. At least the first shaped strip is joined to the second web. The second web is repositioned in the cross machine direction a predetermined distance. At least the second shaped strip is joined to the second web. The resultant composite web is cut into separate shaped components by a separating cut having a pattern defining the edges of each shaped component.

The process of the present invention provides flexibility with respect to the relative positions of the shaped strips in the composite web by repositioning the second web in the cross machine direction. The shaped strips may thus move along paths parallel to the original centerline of the first web from the points where they are cut from the first web to the points where they are joined to the second web. Because cross machine direction movement of the shaped strips is not required, the shaped strips may be processed while lying flat on roll surfaces and any other conveying surfaces. Therefore, the shaped strips may be maintained under good process control.

BRIEF DESCRIPTION OF THE DRAWINGS

While the specification concludes with claims particularly pointing out and distinctly claiming the subject matter which is regarded as the present invention, it is believed that the invention will be better understood from the following description taken in conjunction with the accompanying drawings, in which:

FIG. 11 is a schematic plan view of sequential portions of another alternative exemplary embodiment of the process of the present invention;

FIG. 12 is an enlarged partial view of the first sequential portion of the exemplary embodiment of FIG. 11;

DETAILED DESCRIPTION OF THE INVENTION

The method of the present invention is particularly suited for manufacturing shaped components 200 for use in the manufacture of disposable absorbent articles. As used herein, the term "absorbent article" refers to a device which absorbs and contains body exudates, and more specifically, refers to a device which is placed against the skin of a wearer to absorb and contain the various exudates discharged from the body. The term "disposable" is used herein to describe absorbent articles which are intended to be used once and then discarded. A "unitary" absorbent article refers to an absorbent article which is formed from separate parts united together to form a coordinated entity so that they do not require separate manipulative parts, such as a separate holder and liner. A preferred embodiment of a unitary disposable absorbent article comprising shaped components 200 manufactured by the method of the present invention is the diaper 20 shown in FIG. 1. As used herein, the term "diaper" refers to an absorbent article generally worn by infants and incontinent persons that is generally worn about the lower torso of the wearer. However, that the present invention is also applicable to other absorbent articles such as incontinence briefs, diaper holders, feminine hygiene garments, training pants, pull-on pants, and the like.

Figure 1:
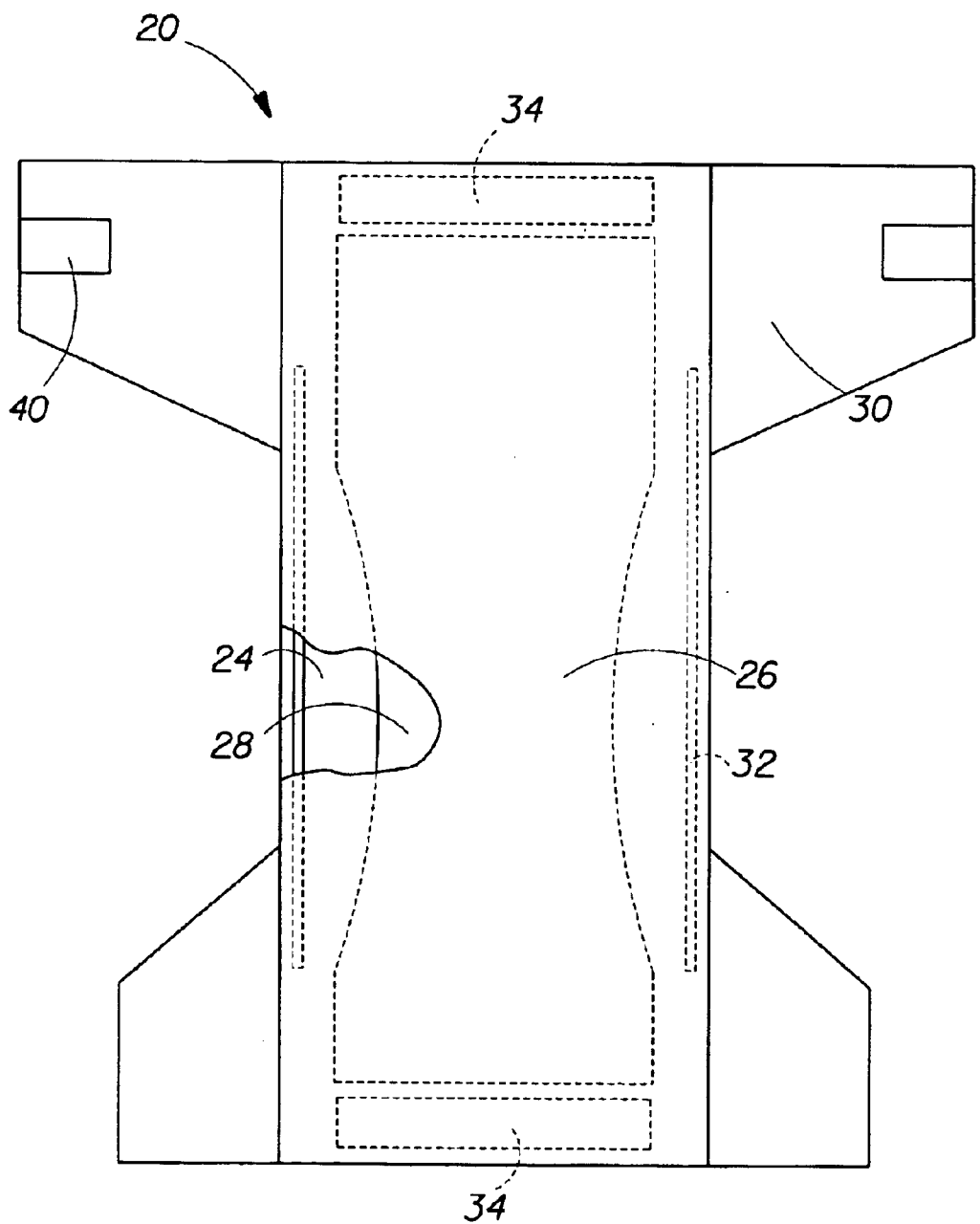
FIG. 1 is a simplified plan view of an absorbent article comprising shaped components made in accordance with the method of the present invention.

With reference to FIG. 1, an absorbent article, such as diaper 20, generally comprises a liquid permeable topsheet 24, a liquid impermeable backsheet 26, and an absorbent core 28 sandwiched between the topsheet 24 and the backsheet 26. The diaper 20 preferably further comprises elasticized leg cuffs 32, side panels 30, an elastic waist feature 34 and a fastening system 40. An example of an absorbent article in which the shaped components 200 of the present invention may be used is described in U.S. Pat. No. 5,580,411, issued to Nease et al. on Dec. 3, 1996, which is hereby incorporated herein by reference.

The shaped components 200 may be produced on the apparatus 10 shown schematically in FIG. 2 through FIG. 6. The apparatus 10 may be integrated into a disposable absorbent article manufacturing line such that the shaped components 200 may be manufactured "on-line". As used herein, the term "integrated" refers to interconnected process modules that operate concurrently to produce finished products from source materials. The term "on-line" is used to refer to the process of manufacturing an element of the finished product on an apparatus that is integrated with the manufacturing line that produces the disposable absorbent article to which the element will be joined.

In a preferred embodiment, each of the webs of the materials making up the shaped components 200 is fed into the apparatus 10 by a web delivery system. The web delivery system preferably feeds the web into the apparatus 10 at a predetermined feed rate, while maintaining a predetermined level of tension. Each web delivery system preferably comprises an unwinder system, a tensioning and metering system, and a tracking device. The tensioning and metering system preferably comprises a tensioning device, such as a dancer, a metering device, such as a powered roll or S-wrap roll pair, and a feedback system to control the speed of the unwinder system. Suitable web delivery systems are available from the Curt G. Joa Corporation of Sheboygan Falls, Wis., U.S.A. The tracking device preferably guides the web to place the centerline of the web exiting the tracking at a predetermined lateral position. A tracking device manufactured by the Fife Corporation of Oklahoma City, Okla., U.S.A., under the trade designation Fife A9 is an example of a suitable tracking device.

Examining the process in greater detail, a first web 140 of the material from which the shaped components 200 are made is first provided to the apparatus 10 in the machine direction. As used herein, the term "machine direction" refers to the general direction of movement of the materials being processed. The machine direction is shown in FIG. 7 through FIG. 15 by the arrow MD, which points downstream along the machine direction. The term "downstream" refers herein to a position or a direction toward the latter steps of the process, relative to another position, while the term "upstream" refers herein to a position or a direction toward the earlier steps of the process, relative to another position, i.e., to the opposite of downstream. The term "cross machine direction" refers to both of the pair of opposing vectors defining an axis generally in the plane of the web material being processed and perpendicular to the machine direction. The term "vertical direction" refers to a direction generally orthogonal to both the machine direction and the cross machine direction.

The first web 140 may comprise a single material or a laminate of suitable materials. For example, in an embodiment in which the process of the present invention is used to make elastically extensible side panels 30, the first web 140 may comprise an elastomeric material, such as BEX501 film or X27222 film, both available from Tredegar Industries, Inc. of Terre Haute, Ind., U.S.A. "Elastically extensible" elements extend in at least one direction when a force is applied and return to approximately their original dimensions after the force is removed. In general, suitable materials for the first web 140 include materials used in other elements of the diaper 20, such as topsheet 24 material, backsheet 26 material, waist feature 34 material, side panel 30 material, elastic strip material, and the like. In some embodiments, the first web 140 may comprise, for example, film, formed film, scrim material, foam, strip material, or any other suitable material. In a laminate form, the first web 140 may include, for example, nonwoven material, film, formed film, scrim material, foam, and/or strip material.

In some embodiments, such a laminate form of the first web 140 may comprise an activated material. As used herein, the term "activated" refers to a material which has been mechanically deformed so as to impart elastic extensibility to the material. The material may be activated by any of several means including, but not limited to, ring rolling, embossing, thermoforming, high pressure hydraulic forming, or casting. Embodiments of the present invention are contemplated wherein the first web 140 may comprise additional elastomeric materials such as elastic, natural or synthetic rubber, rubber foams, elastomeric scrims, woven or nonwoven elastomeric webs, elastomeric composites, zero-strain stretch laminates, prestrained stretch laminates or the like.

Figure 7:
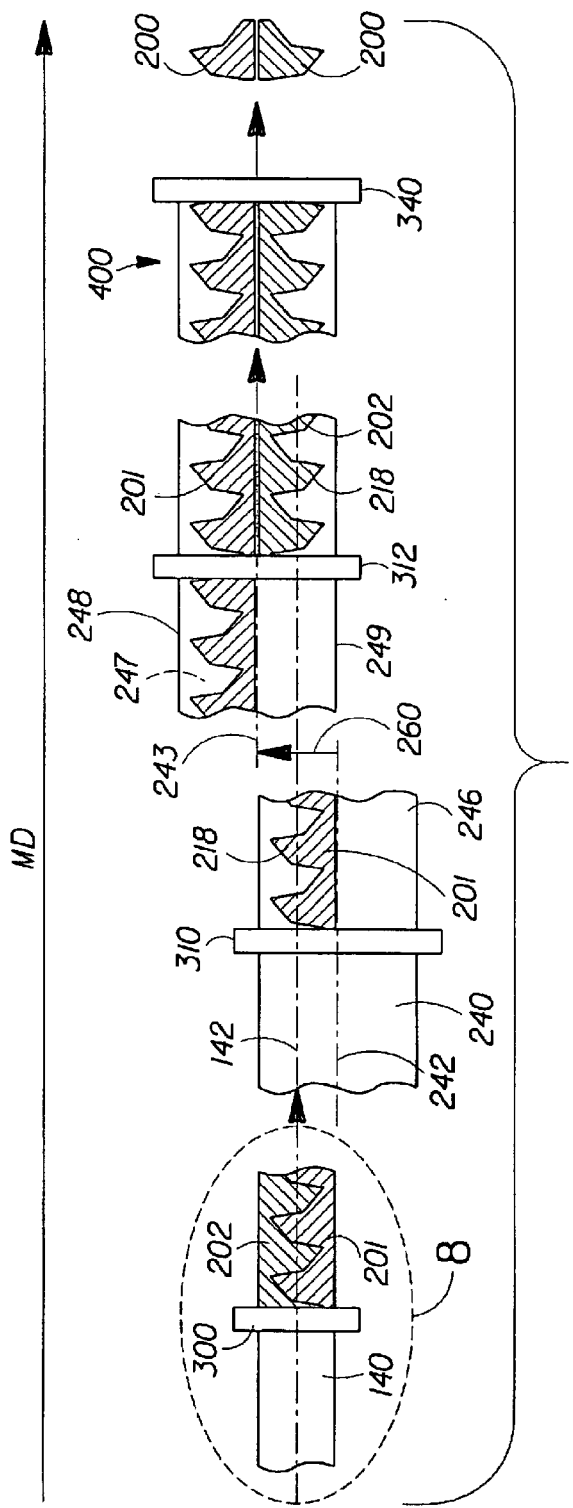
FIG. 7 is a schematic plan view of sequential portions of an exemplary embodiment of the process of the present invention.
Figure 8:
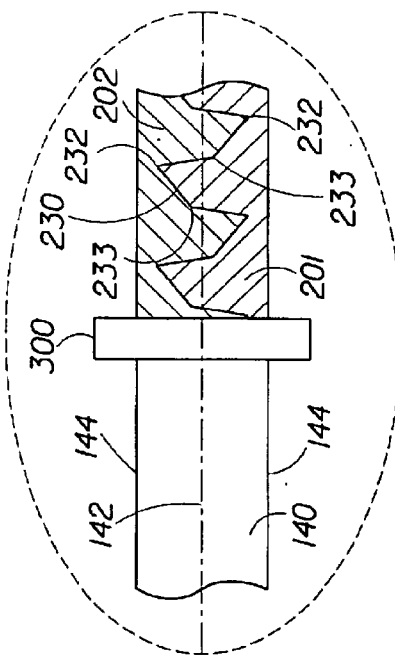
FIG. 8 is an enlarged partial view of the first sequential portion of the exemplary embodiment of FIG. 7.

The first web 140 is cut to form a first shaped strip 201 and a second shaped strip 202, as shown in FIG. 7 and FIG. 8. The pattern 230 of the shaping cut extends in the machine direction and alternately extends in the cross machine direction to alternate distal points 232 located between the longitudinal side edges 144 of the first web 140. Therefore, the shaping cut pattern 230 defines the shaped strips, each of which remains continuous in the machine direction. The alternating shaping cut forms alternating projecting portions 218 of the shaped strips which are nested, fitting compactly together along the alternating cut. The shaping cut pattern 230 may be continuous or may be intermittent, e.g., in the form of perforations adequate for the later separation of the shaped strips.

The shaping cut pattern 230 may form sets of nested shaped strips which are laterally or longitudinally symmetric or asymmetric. As used herein, the term "lateral" refers to the cross machine direction and the term "laterally symmetric" refers to symmetry about a line parallel to the machine direction. Also, the term "longitudinal" refers herein to the machine direction and the term "longitudinally symmetric" refers to symmetry about a line parallel to the cross machine direction. The term "set" refers herein to the contiguous nested shaped strips formed by one or more shaping cut patterns 230. Thus, in some embodiments, the set is the pair of nested shaped strips formed by a single shaping cut pattern 230. In other embodiments, the set comprises the three or more contiguous nested shaped strips formed by two or more shaping cut patterns 230.

For example, the pair of nested shaped strips of the exemplary embodiment shown in FIG. 7 and FIG. 8 is laterally symmetric, because the shape of the second shaped strip 202 is a mirror image of the shape of the first shaped strip 201, the shape being mirrored about the centerline 142 of the first web 140. Note that it is sufficient for lateral symmetry that the shapes of the shaped strips be lateral mirror images; it is not necessary that these shapes be matched in phase while the shaped strips are nested together. The lateral symmetry in this embodiment can be seen most easily in FIG. 7 at the point where the first shaped strip 201 and second shaped strip 202 are matched in phase downstream of second combining roll 312. The pair of nested shaped strips in the embodiment shown in FIG. 7 and FIG. 8 is longitudinally asymmetric, because the shapes of the first shaped strip 201 and second shaped strip 202 are not mirror images of each other about any cross machine direction line.

Furthermore, in this embodiment, the first shaped strip 201 and second shaped strip 202 have a common machine direction orientation. The term "machine direction orientation" refers herein to the relative machine direction position of elements of a shaped strip. Shaped strips having geometrically similar elements positioned geometrically similarly in the machine direction have a common machine direction orientation. For example, in this embodiment, the distal points 232 of each of the projecting portions 218 of both the first shaped strip 201 and second shaped strip 202 are located downstream of the intermediate points 233. Therefore, the first shaped strip 201 and second shaped strip 202 have a common machine direction orientation, in this embodiment.

Considering the exemplary embodiment shown in FIG. 11 and FIG. 12, the first shaping cut pattern 234 forms the nested pair of the first shaped strip 201 and second shaped strip 202 from the first panel 220. This nested pair is both laterally and longitudinally asymmetric, because the shapes of the first shaped strip 201 and second shaped strip 202 are not mirror images of each other about any machine direction line or about any cross machine direction line. The shaped strips in this first panel 220 of this embodiment have opposing machine direction orientations, because the distal edge 231 of each of the projecting portions 218 of the first shaped strip 201 is generally upstream of the proximal portion 235 of each of its projecting portions 218, while the distal edge 231 of each of the projecting portions 218 of the second shaped strip 202 is generally downstream of the proximal portion 235 of each of its projecting portions 218. The second shaping cut pattern 236 forms the nested pair of the third shaped strip 203 and the fourth shaped strip 204 from the second panel 222. Like the nested pair of shaped strips in the first panel 220, this nested pair is also laterally and longitudinally asymmetric, and the shaped strips in this second panel 222 also have opposing machine direction orientations.

Also, the nested pair of shaped strips formed from the first panel 220 and the nested pair of shaped strips formed from the second panel 222 in this embodiment have different axial orientations. The term "axial orientation" refers herein to the angle, relative to the downstream machine direction, defined by the axis of symmetry of each of the projecting portions 218 of a shaped strip, when viewed in plan. In particular, in this embodiment, the axis of symmetry 219 of the first shaped strip 201 defines an acute clockwise angle relative to the downstream machine direction, while the axis of symmetry of the third shaped strip 203 defines an acute counterclockwise angle relative to the downstream machine direction.

In other embodiments, also, the set of nested shaped strips may have opposing machine direction orientations. For example, a shaping cut pattern 230 may have, between distal points, successive cross machine direction segments which alternate in orientation between parallel to the cross machine direction and diagonal, e.g., alternate in a zigzag. In such a zigzag embodiment, the downstream edge of each of the projecting portions 218 of a first shaped strip 201 may be parallel to the cross machine direction, in which case the upstream edge of each of the projecting portions 218 of a second shaped strip 202, nested with the first shaped strip 201, would also be parallel to the cross machine direction, while the downstream edge of each of the projecting portions 218 of the second shaped strip 202 would be diagonally oriented. Therefore, the resultant nested shaped strips would have opposing machine direction orientations in this and any similar embodiment.

Embodiments in which the nested shaped strips have opposing machine direction orientations may present certain advantages or disadvantages, depending on the application. For example, in order to position the resultant shaped components 200 adjacent a diaper 20 web as lateral mirror images of each other, i.e., as laterally opposed shaped components 200 having a common machine direction orientation, it would be necessary to reorient either the first shaped strip 201 or second shaped strip 202 prior to separating the shaped components 200, or it would be necessary to reorient one of the shaped components 200 after separating them. This reorientation could be accomplished by, for example, separating the nested shaped strips, winding up one of the shaped strips, reorienting the wound roll containing the shaped strip, and subsequently unwinding the shaped strip. However, these extra steps add complexity and cost, in comparison to an embodiment in which the shaped strips, and therefore the shaped components 200, have a common machine direction orientation throughout the process of the present invention. On the other hand, opposing machine direction orientations may be advantageous in embodiments in which shaped strips having opposing machine direction orientations are combined to form multi-directional shaped components 200, such as the exemplary embodiment of FIG. 11, which is described below.

Figure 13:
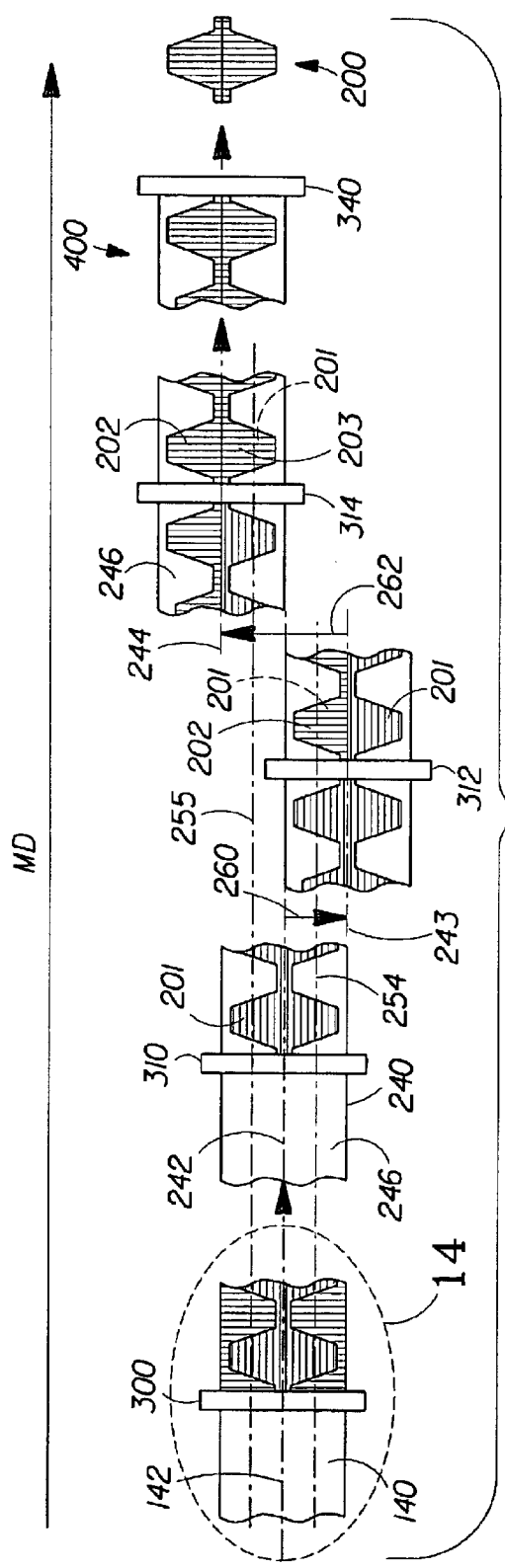
FIG. 13 is a schematic plan view of sequential portions of another alternative exemplary embodiment of the process of the present invention.
Figure 14:
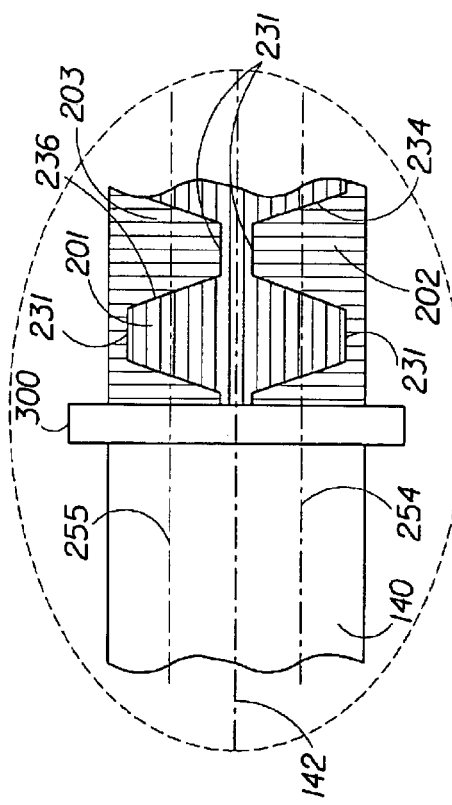
FIG. 14 is an enlarged partial view of the first sequential portion of the exemplary embodiment of FIG. 13.

As another example, the set of three nested shaped strips of the embodiment shown in FIG. 13 and FIG. 14 is both laterally and longitudinally symmetric. The shape of the first shaped strip 201 in this exemplary embodiment is symmetric about the centerline 142 of the first web 140 and the shape of the third shaped strip 203 is a mirror image of the shape of the second shaped strip 202. The set of three nested shaped strips is longitudinally symmetric, because the contours are mirrored about a cross machine direction line intersecting the midpoints of any pair of opposing distal edges 231. In addition, none of the three shaped strips has a machine direction orientation, i.e., the points of both shaping cut patterns repeat identically in the machine direction.

The cutting of the first web 140 may be accomplished in many ways. For example, in the exemplary embodiment of the apparatus 10 shown in FIG. 2, the alternating shaping cut may be made by a die cutter 300. Such a die cutter 300 typically has a die roll 302 and an anvil roll 304. A vacuum may be provided and the anvil roll 304 may have vacuum holes which hold the first web 140 in place while it is cut and which hold the shaped strips in place until the points in the process when they are directed away from the anvil roll 304. In some embodiments, the anvil roll 304 may have an electrostatic device which holds the first web 140 and the shaped strips in place. Likewise, in some embodiments, portions of the anvil roll 304 surface may have high friction areas or some other suitable element which controls the movement of the first web 140 and the shaped strips while on the surface of the anvil roll 304. The first web 140 may also be cut by other cutting means, such as a shear cutter, a water jet cutter, a laser cutter, and any other cutting means suitable for cutting the material to be shaped.

The shaped strips are separated after being cut from the first web 140. In the exemplary embodiment of the apparatus 10 shown in FIG. 2, the separation is accomplished by routing the second shaped strip 202 away from the surface of the die cutter anvil roll 304 onto the surface of the second transfer roll 308, while continuing to hold the first shaped strip 201 on the surface of the anvil roll 304 until it is directed away from the anvil roll 304 onto the first transfer roll 306. Like the die cutter anvil roll 304, each of the transfer rolls may have vacuum holes, an electrostatic device, or some other suitable element which controls the movement of the respective shaped strip while on the surface of the transfer roll.

The first shaped strip 201 preferably is released from the surface of the anvil roll 304 and transferred to the surface of the first transfer roll 306 without a loss of control of the first shaped strip 201. Such a release can be accomplished by, for example, providing a vacuum to vacuum holes on the anvil roll 304 until a predetermined point and then relieving the vacuum at that point. The point of release may be located where a line between the centers of the anvil roll 304 and first transfer roll 306 intersects the surface of the anvil roll 304. Similarly, such a transfer can be accomplished by providing a vacuum to vacuum holes on the first transfer roll 306, starting from the intersection of the same line between roll centers with the surface of the first transfer roll 306, and continuing around the first transfer roll 306 to a predetermined point where the first shaped strip 201 is directed away. In general, any components suitable for the material involved may be used in the apparatus 10 to accomplish such a release and transfer of the first shaped strip 201, with control.

A second web 240 of the material to which the shaped strips are to be joined is provided to the apparatus 10 in the machine direction. The second web 240 may comprise a single material or a laminate of suitable materials. For example, in an embodiment in which the process of the present invention is used to make elastically extensible side panels 30, the second web 240 may comprise a nonwoven material, such as P-14 nonwoven available from Fiberweb North America, Inc. of Greenville, S.C., or FPN332D nonwoven available from BBA Nonwovens of Simpsonville, S.C., U.S.A. Other suitable nonwovens include, but are not limited to, those comprising natural fibers such as cotton or wool; synthetic fibers of nylon, polyamides, polyesters, or polyolefins; yarns; polyethylene; polypropylene; or any combination of these or other materials known in the art. The second web 240 may likewise comprise materials such as those described above with regard to the first web 140 materials.

The second web 240 may be provided to the apparatus 10 with its centerline 242 in the same cross machine direction position as the centerline 142 of the first web 140 or with its centerline 242 offset in the cross machine direction from the centerline 142 of the first web 140. For example, a second web 240 of greater width than the first web 140 may be provided with its centerline 242 offset such that the first shaped strip 201 is joined to the second web 240 adjacent a first longitudinal edge 248 of the second web 240. In other embodiments, the second web 240 may be provided with its centerline 242 offset such that the first shaped strip 201 is joined to the second web 240 in another position, such as on the centerline 242 of the second web 240, adjacent a second longitudinal edge 249 of the second web 240, or in another position.

A first surface 210 of the first shaped strip 201 is joined to a first surface 246 of the second web 240 at a first combining point 311. At the first combining point 311, the first shaped strip 201 and the second web 240 are brought into sufficiently close proximity for joining. As used herein, the term "joined" encompasses configurations where an element is directly secured to another element, as well as configurations where an element is indirectly secured to another element by affixing one element to an intermediate member or members that are, in turn, affixed to the other element. The first shaped strip 201 and the second web 240 may be joined continuously or intermittently by any means known in the art including, but not limited to, heat bonding, pressure bonding, adhesive bonding, dynamic mechanical bonding, ultrasonic bonding or any combination of these means. In the embodiment shown in FIG. 2, for example, the first shaped strip 201 and the second web 240 are joined with an adhesive which is applied onto the second web 240 by means of a first adhesive applicator 332. An example of a suitable joining adhesive is a spiral coating of 2031 adhesive, available from Bostik Findley, Inc., of Middleton, Mass., U.S.A. In this embodiment, a first combining roll 310 conveys the second web 240 to the first combining point 311 and provides sufficient compressive force to effect the adhesive bond between the first shaped strip 201 and the second web 240.

An outer surface of the first combining roll 310 may have areas of surface relief, ie., areas which are raised or recessed with respect to each other or to other areas. These areas of surface relief may be shaped to correspond to the shape of the first shaped strip 201. Such a first combining roll 310 with surface relief may be matched in phase with the first shaped strip 201 such that the raised areas may press together predetermined portions of the first shaped strip 201 and the second web 240, while the surrounding recessed areas exert less or no pressure on the materials being processed. In some embodiments, such a relieved combining roll preferably is close coupled or driven from the same drive as the die cutter 300 to facilitate keeping the combining roll in phase with the shaping cut pattern 230, and therefore with the shaped strip.

After the joining of the first shaped strip 201 and the second web 240, the second web 240 is repositioned in the cross machine direction a predetermined distance 260 while moving along a web path from the first combining point 311 to a second combining point 313. As will become clearer in the description below, the distance 260 by which the second web 240 is repositioned defines the cross machine direction relative positions of the first shaped strip 201 and second shaped strip 202 in the resultant composite web 400. The cross machine direction repositioning can be achieved in a variety of ways. For example, as shown in FIG. 2 and FIG.

3, the second web 240 may be routed over a series of rollers and turning devices configured such that the second web 240 arrives at the second combining point 313 in the desired cross machine direction position. With the use of rollers and turning devices, the second web 240 may be repositioned while continuously moving in the machine direction at a substantially uniform linear velocity. Therefore, process parameters such as the tension and tracking of the second web 240 may be maintained between the first combining point 311 and the second combining point 313.

Figure 2:
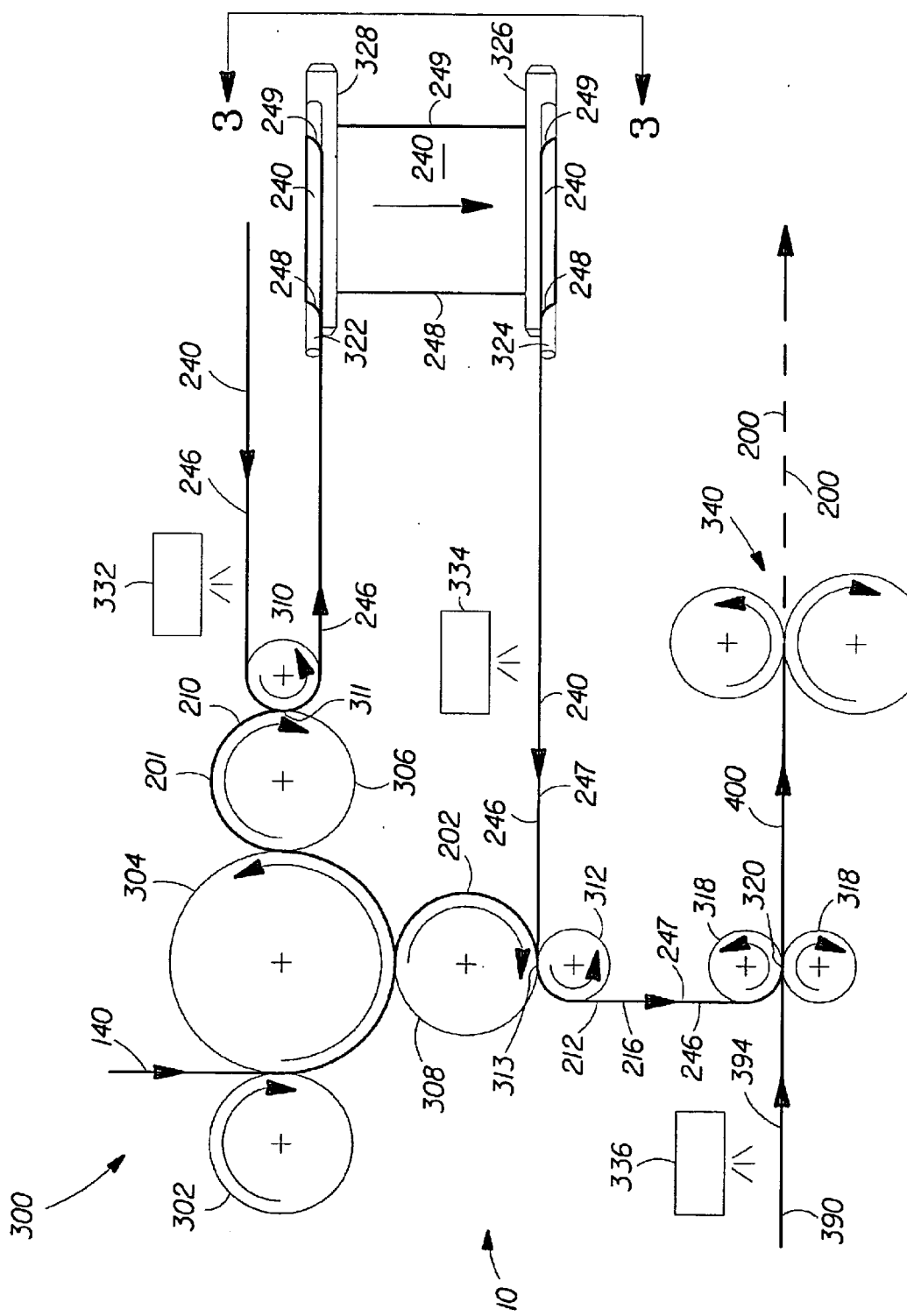
FIG. 2 is a schematic elevation view of an exemplary embodiment of the process of the present invention.
Figure 3:
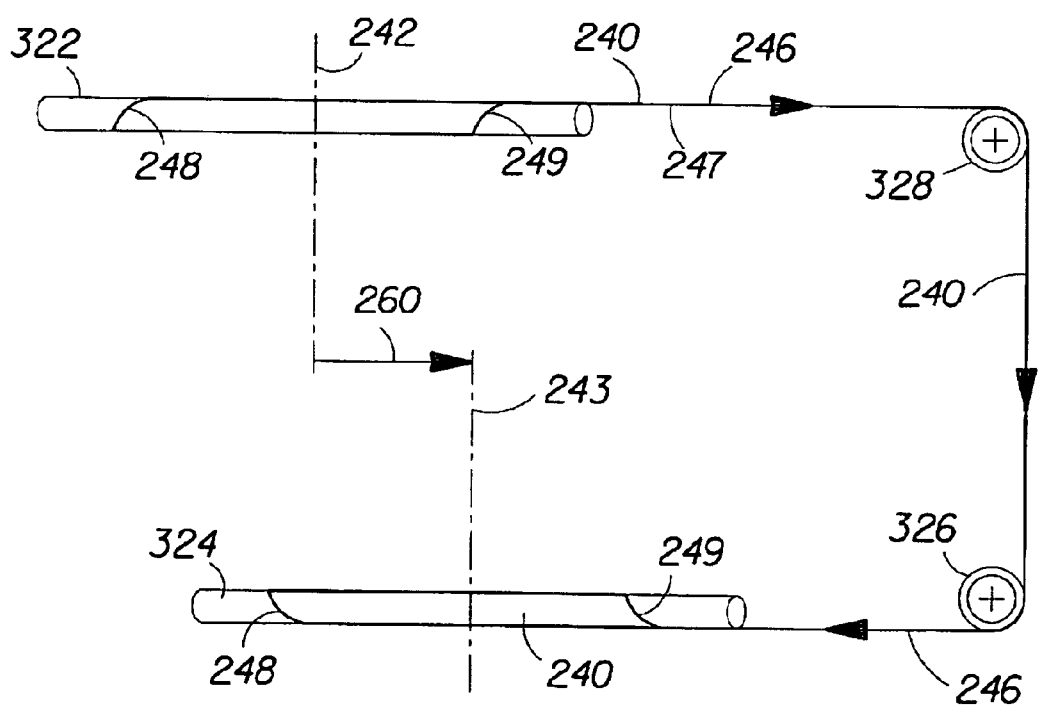
FIG. 3 is a schematic elevation view of a portion of the process embodiment of FIG. 2, showing the repositioning of the second web in the cross machine direction.

In the particular embodiment shown in FIG. 2 and FIG. 3, the second web 240 is routed from the first combining point 311, where it is positioned on an original centerline 242, over a first 45 degree turning bar 322, a driven roller 326, an idler roller 328, and a second 45 degree turning bar 324 to a repositioned centerline 243, and then to a second combining roll 312 at the second combining point 313. In this embodiment, the first 45 degree turning bar 322 turns the second web 240 ninety degrees from the machine direction to the cross machine direction. The driven roller 326 provides a driving force to pull the second web 240 over the stationary first turning bar 322 and turns the web from the cross machine direction to the vertical direction. The idler roller 328 turns the second web 240 from the vertical direction to the cross machine direction and the second turning bar 324 turns the second web 240 ninety degrees from the cross machine direction back to the machine direction. The repositioning distance 260 is defined by the cross machine direction offset of the second turning bar 324 relative to the first turning bar 322. When the cross machine direction offset of the turning bars is zero, the repositioned centerline 243 of the second web 240 at the second combining point 313 is at the same cross machine direction position as the original centerline 242 at the first combining point 311.

A first surface 214 of the second shaped strip 202 is joined to the second web 240 at the second combining point 313. In the embodiment shown in FIG. 2, for example, the first surface 214 of the second shaped strip 202 is the radially outboard surface of the shaped strip while on the surface of the second transfer roll 308. At the second combining point 313, the second shaped strip 202 and the second web 240 are brought into sufficiently close proximity for joining. The second shaped strip 202 and the second web 240 may be joined as described above with respect to joining the first shaped strip 201 and the second web 240. In the embodiment shown in FIG. 2, for example, the second shaped strip 202 and the second web 240 are joined with an adhesive which is applied onto the second web 240 by means of a second adhesive applicator 334. In this embodiment, a second combining roll 312 conveys the second web 240 to the second combining point 313 and provides sufficient compressive force to effect the adhesive bond between the second shaped strip 202 and the second web 240.

Figure 4:
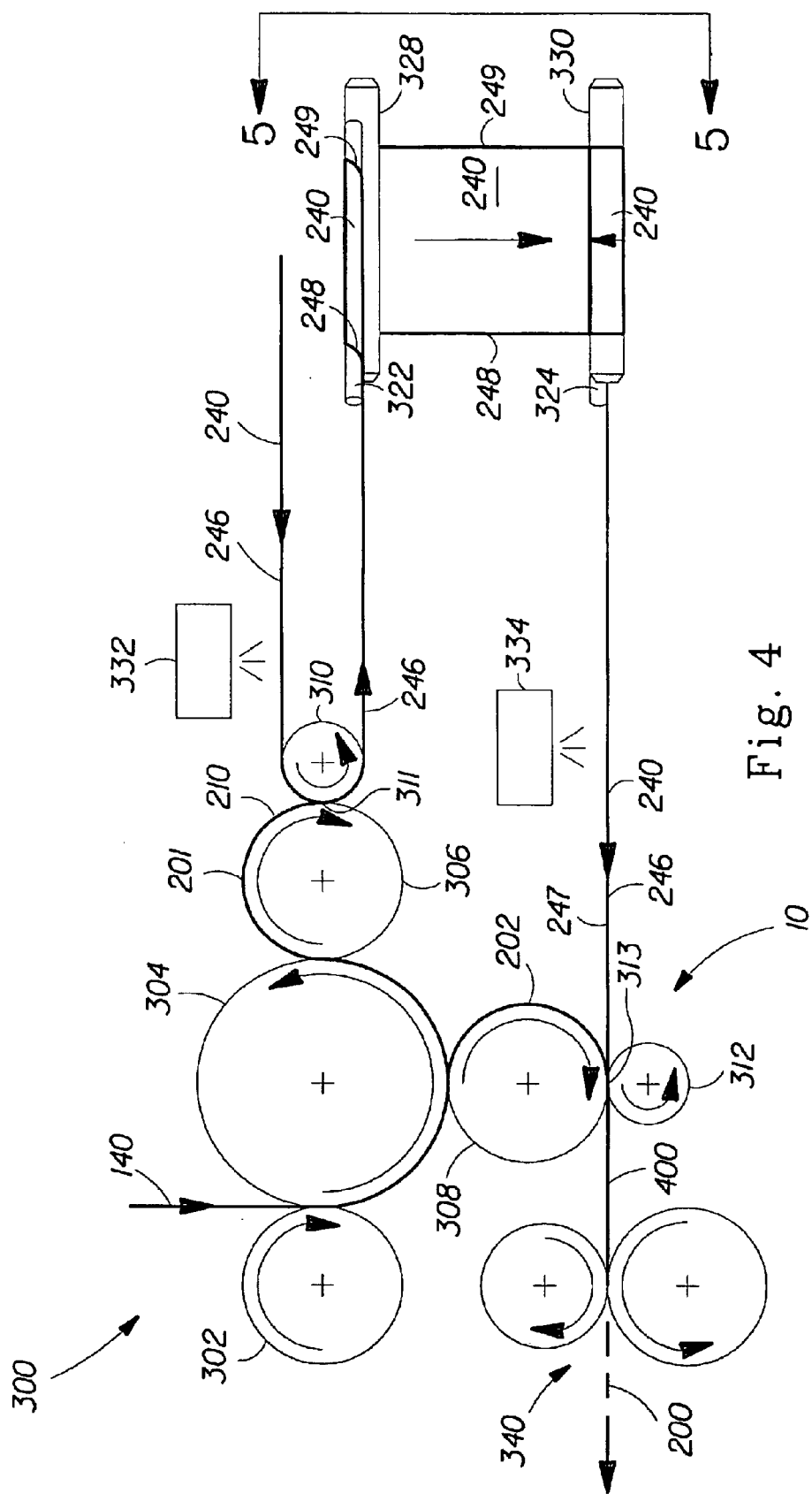
FIG. 4 is a schematic elevation view of an alternative exemplary embodiment of the process of the present invention.

In the embodiment shown in FIG. 2, both the first shaped strip 201 and the second shaped strip 202 are joined to the same surface of the second web 240. In other embodiments, such as that shown in FIG. 4, for example, the first shaped strip 201 may be joined to a first surface 246 of the second web 240 and the second shaped strip 202 may be joined to a second surface 247 of the second web 240. Such an embodiment includes means for routing the second web 240 differently from the embodiment of FIG. 2. For example, a reversing idler roller 330 may be used in the web path for reversing the vertical orientation of the opposing surfaces of the second web 240, as shown in the exemplary embodiment of FIG. 4 and FIG. 5. A comparison of the Figures shows that, in FIG. 2 and FIG. 3, the first surface 246 of the second web 240 is oriented "upward", while in FIG. 4 and FIG. 5, the first surface 246 of the second web 240 is oriented "downward". Since the vertical orientation of the other process elements is the same in all of these Figures, it can be seen that the vertical orientation of the opposing surfaces of the second web 240 is reversed by the reversing idler roller 330 of FIG. 4 and FIG. 5. Thus, as shown in the embodiment of FIG. 4, for example, the first shaped strip 201 may be joined on the first surface 246 of the second web 240, the vertical orientation of the second web 240 may be reversed, and the second shaped strip 202 may then be joined on the second surface 247 of the second web 240.

As mentioned above, the distance 260 by which the second web 240 is repositioned in the cross machine direction between the first combining point 311 and second combining point 313 defines the cross machine direction relative positions of the first shaped strip 201 and second shaped strip 202 in the resultant composite web 400. The reason for this can now be seen, in that the cross machine direction position of the second web 240 at the second combining point 313 defines where the second shaped strip 202 will be joined onto the second web 240. The cross machine direction repositioning can be in either cross machine direction, i e., "left" or "right" with respect to the centerline 242 of the second web 240 at the first combining point 311. Thus, the second shaped strip 202 may be joined onto the second web 240 to the "left" or "right" of the first shaped strip 201, or may be joined partially or wholly overlapping the first shaped strip 201 in the cross machine direction.

The process of the present invention makes this flexibility with respect to the relative positions of the shaped strips in the composite web 400 possible by repositioning the second web 240 in the cross machine direction. The shaped strips may thus move along paths parallel to the original centerline 142 of the first web 140 from the points where they are cut from the first web 140 to the points where they are joined to the second web 240. Because cross machine direction movement of the shaped strips is not required, the shaped strips may be processed while lying flat on roll surfaces and any other conveying surfaces. Therefore, the shaped strips may be maintained under good process control throughout the process.

Figure 9:
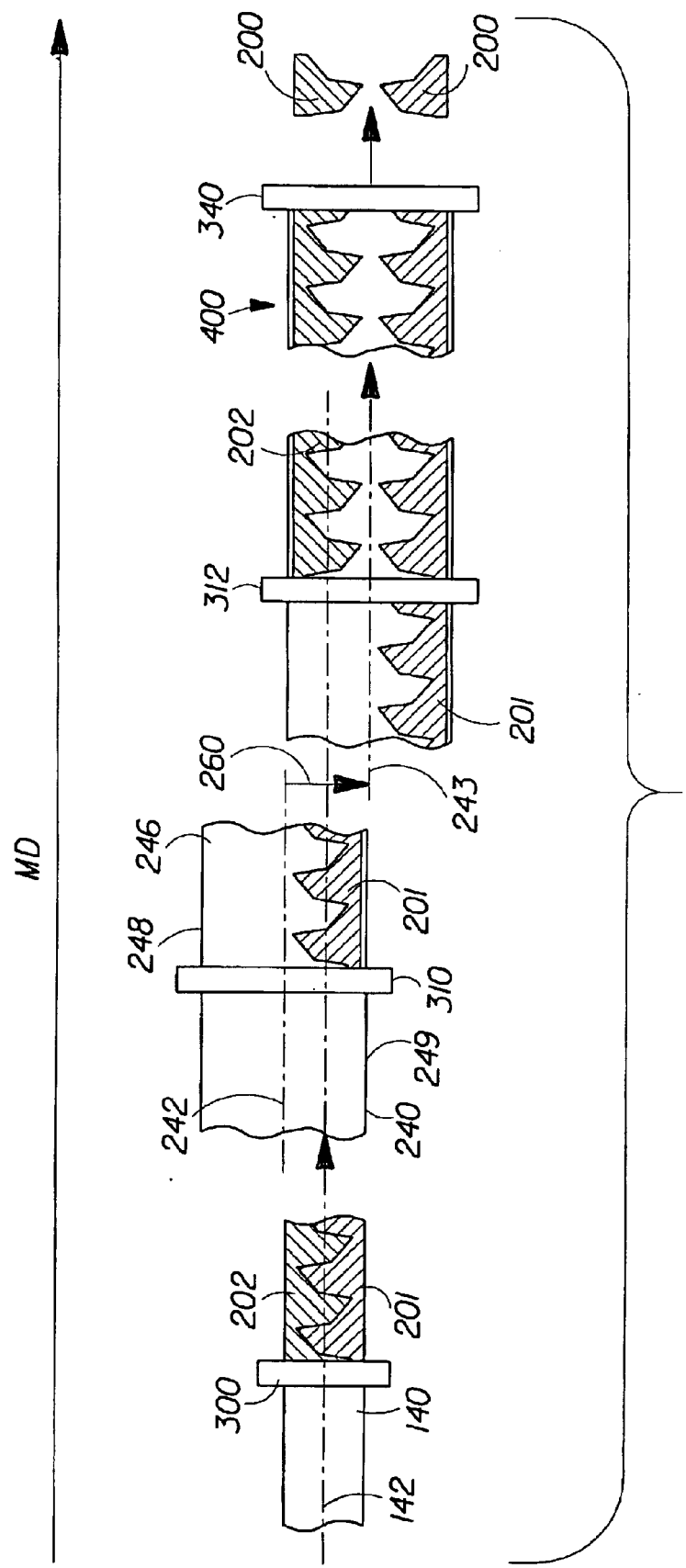
FIG. 9 is a schematic plan view of sequential portions of an alternative exemplary embodiment of the process of the present invention.

In the embodiment shown in FIG. 2, the projecting portions 218 of the shaped strips continue to project in their original directions, i.e., their directions as cut from the first web 140, in the composite web 400. Specifically, the projecting portions 218 of the first shaped strip 201 and second shaped strip 202 continue to project in the same opposing cross machine directions at the second combining point 313 as when they were originally cut on the surface of the anvil roll 304. Therefore, the shaped strips and the second web 240 may be joined as shown in FIG. 7, with the projecting portions 218 projecting outwardly with respect to the centerline of the composite web 400. In another embodiment, the shaped strips and the second web 240 may be joined as shown in FIG. 9 with the projecting portions 218 projecting inwardly with respect to the centerline of the composite web 400.

Figure 5:
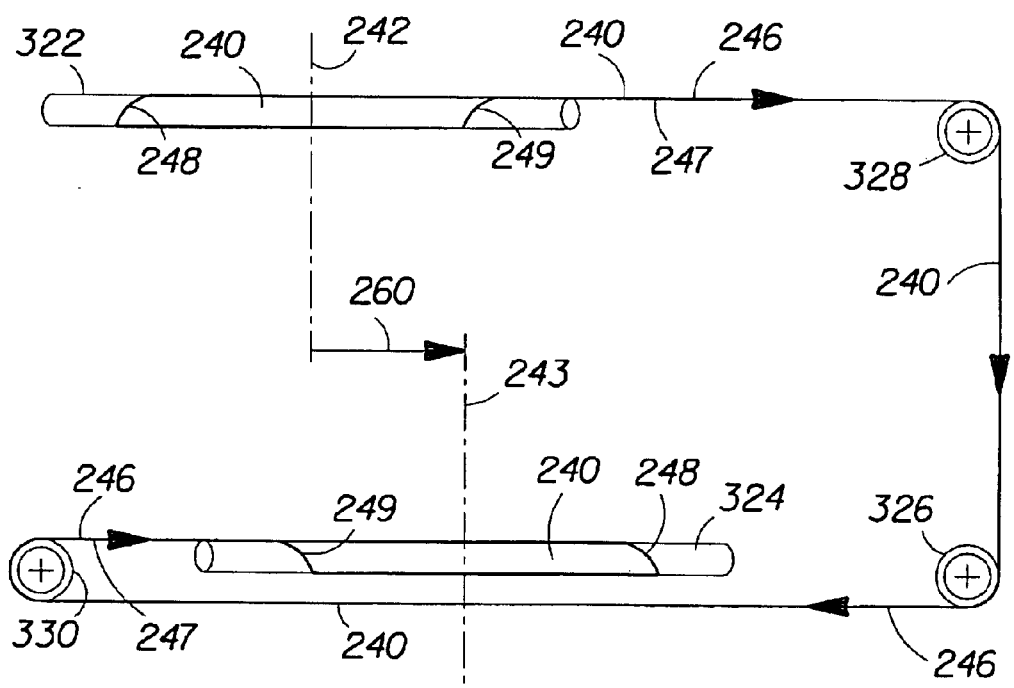
FIG. 5 is a schematic elevation view of a portion of the process embodiment of FIG. 4, showing the repositioning of the second web in the cross machine direction and the vertical reorientation of the second web.
Figure 6:
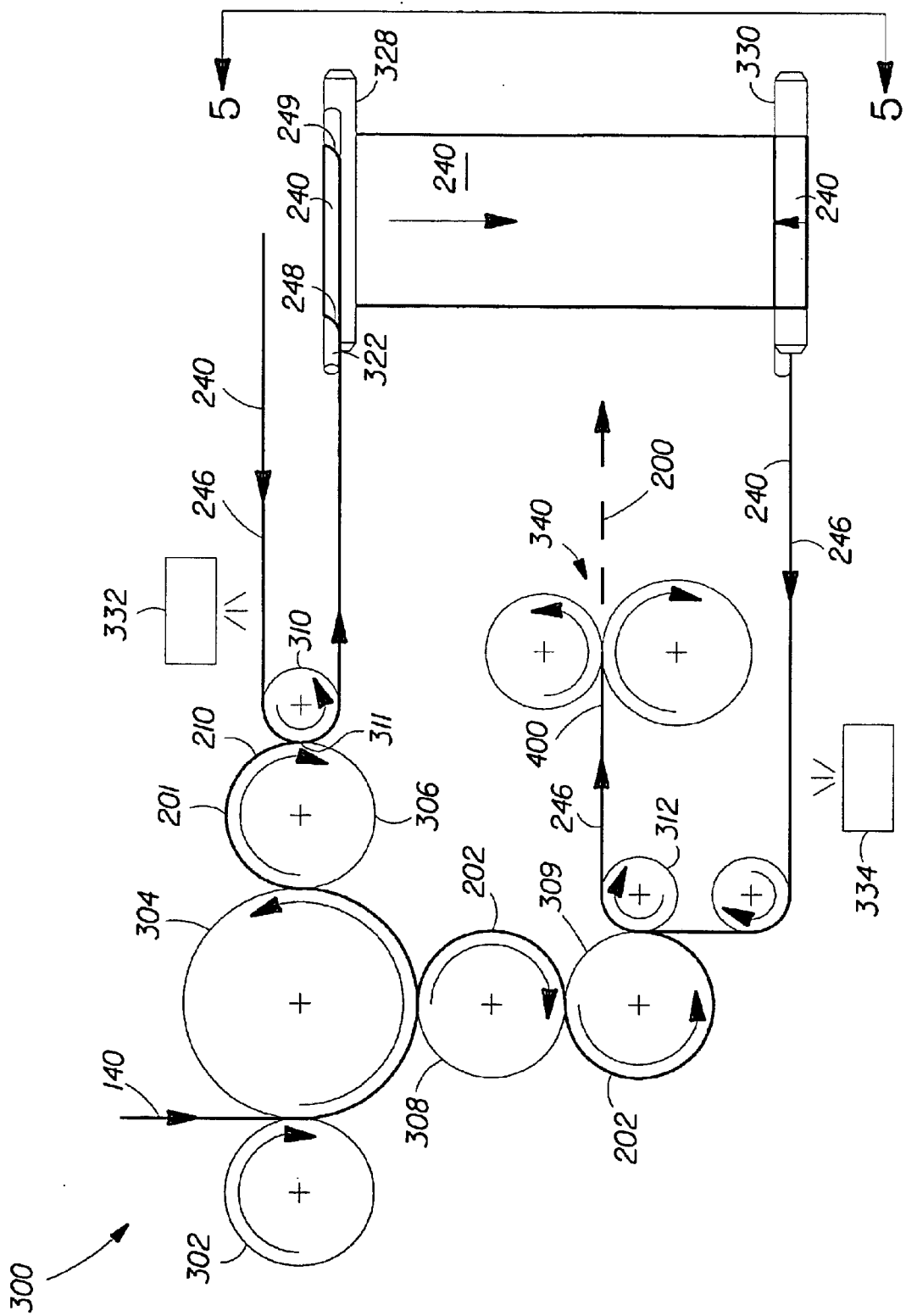
FIG. 6 is a schematic elevation view of another alternative exemplary embodiment of the process of the present invention.

In other embodiments, such as that shown in FIG. 4 and FIG. 5, the shaped strips and the second web 240 may be joined with the projecting portions 218 of the first shaped strip 201 and the second shaped strip 202 projecting in the same direction. In this exemplary embodiment, the reversing idler roller 330 makes this result possible. As described above, the vertical orientation of the opposing surfaces of the second web 240 is reversed by the reversing idler roller 330. At the same time, the cross machine direction orientation of the second web 240 is also reversed by the reversing idler roller 330. A comparison of the Figures shows that, in all of FIG. 2, FIG. 3, FIG. 4, and FIG. 5, the first longitudinal edge 248 of the second web 240 is oriented toward the "left" as the second web 240 passes over the first turning bar 322 and downward from the idler roller 328 toward the driven roller 326. In FIG. 3, the first longitudinal edge 248 remains oriented toward the "left" as the second web 240 passes over the second turning bar 324. However, in FIG. 5, the first longitudinal edge 248 is oriented toward the "right", while the second longitudinal edge 249 is oriented toward the "left", as the second web 240 passes over the second turning bar 324. Since the vertical and cross machine direction orientation of the other process elements is the same in all of these Figures, it can be seen that the cross machine direction orientation of the longitudinal edges of the second web 240 is reversed by the reversing idler roller 330 of FIG. 4 and FIG. 5.

Figure 10:
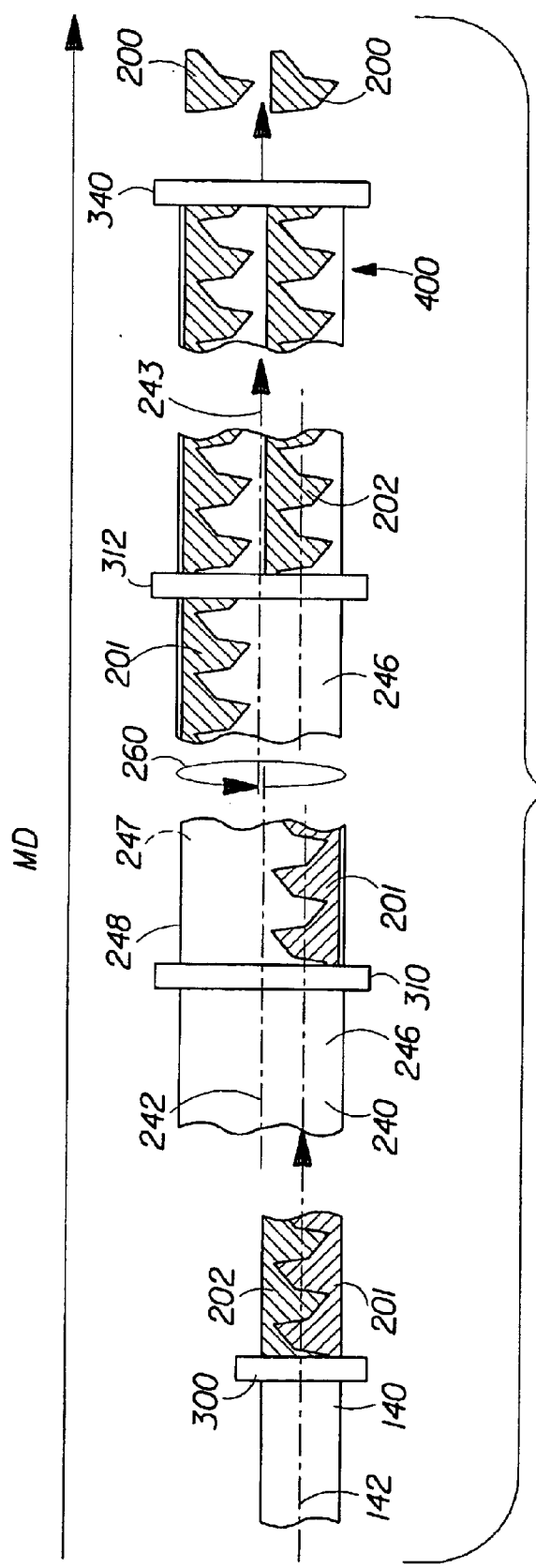
FIG. 10 is a schematic plan view of sequential portions of another alternative exemplary embodiment of the process of the present invention.

Thus, in an embodiment such as that of FIG. 10, for example, the first shaped strip 201 may be joined to the second web 240 with its projecting portions 218 projecting toward the centerline 242 of the second web 240, the cross machine direction orientation of the second web 240 may be reversed, and the second shaped strip 202 may then be joined with its projecting portions 218 projecting in the same direction as the projecting portions 218 of the reversed first shaped strip 201. In the embodiment of FIG. 10, in particular, the first shaped strip 201 and the second shaped strip 202 are both joined on the first surface 246 of the second web 240, with their projecting portions 218 projecting in the same direction. This result may be accomplished by using the exemplary embodiment of FIG. 6, in which the second shaped strip 202 is first transferred from the die cutter anvil roll 304 to the second transfer roll 308 and then to a third transfer roll 309. The second combining roll 312 conveys the second shaped strip 202 to the second combining point 313 adjacent the third transfer roll 309, where the second shaped strip 202 is joined to the second web 240. Alternatively, the shaped strips may be joined to opposing surfaces of the second web 240 with their projecting portions 218 projecting in the same direction, as shown in FIG. 4, in which the first shaped strip 201 is joined on the first surface 246 of the second web 240 and the second shaped strip 202 is joined on the second surface 247 of the second web 240.

The length of the web path between the first combining point 311 and the second combining point 313 defines the phase relationship of the first shaped strip 201 and second shaped strip 202 in the composite web 400. In embodiments in which the die cut pattern 230 is cyclically identical, any projecting portion 218 of the first shaped strip 201 can be paired with any projecting portion 218 of the second shaped strip 202 for phasing purposes. In particular, in some embodiments, the web path length may be such that the projecting portions 218 of the first shaped strip 201 arrive at the second combining point 313 in matched phase with the projecting portions 218 of the second shaped strip 202, as shown in FIG. 7. In other embodiments, the web path length may be such that the projecting portions 218 of the first shaped strip 201 arrive at the second combining point 313 in mismatched phase with the projecting portions 218 of the second shaped strip 202. Thus, the second shaped strip 202 may be joined onto the second web 240 either advanced or retarded relative to the first shaped strip 201, or may be joined partially or wholly overlapping the first shaped strip 201 in the machine direction. Any particular phase relationship may be desirable, depending on the use planned for the composite web 400 after it is made in the process of the present invention. For example, matching the phase of the projecting portions 218 of the first shaped strip 201 and second shaped strip 202 may facilitate the subsequent cutting, spacing, and application of the shaped components 200 onto a diaper web.

In some embodiments, a third web 390 of a material may be provided to the apparatus 10 in the machine direction, for example, as shown in FIG. 2. The third web 390 may comprise materials such as those described above with regard to the first web 140 and second web 240. The third web 390 may be provided with its centerline aligned with the centerline 142 of the first web or the centerline 242 of the second web 240 or with its offset in the cross machine direction from that of either of the first web 140 or second web 240. In the embodiment of FIG. 2, a first surface 394 of the third web 390 is joined to the second web 240 and to second surface 212 of the first shaped strip 201 and to second surface 216 of the second shaped strip 202 at a third web combining point 320, between third web combining rolls 318. The third web 390 and the second web 240 thus sandwich the shaped strips between them, in this embodiment. Alternative embodiments are envisioned in which more than three webs are combined to form the composite web 400. For example, a fourth web may be provided and combined to form a composite web 400 having the first shaped strip 201 sandwiched between the second web 240 and third web 390, and the second shaped strip 202 sandwiched between the third web 390 and fourth web.

The process of the present invention may also be used to make a composite web 400 comprising more than two shaped strips of a first web 140 material. In the embodiment shown in FIG. 11, for example, the first web 140 is cut into four shaped strips as shown in FIG. 12 and the shaped strips are combined to form multi-directional shaped components 200. Multi-directional shaped components comprise elements having different axial orientations. Examples of such multi-directional shaped components are bi-directional extensible side panels, such as those described in U.S. Pat. No. 5,705,013, issued to Nease et al. on Jan. 6, 1998, which is hereby incorporated herein by reference. In this exemplary embodiment, the first web 140 is cut by three cut patterns extending in the machine direction and spaced in the cross machine direction. The first shaping cut pattern 234 and the second shaping cut pattern 236 alternate, as described above, and the dividing cut pattern 238 is positioned between the first shaping cut pattern 234 and the second shaping cut pattern 236. The resultant shaped webs may thus comprise a first panel 220 including the first shaped strip 201 and second shaped strip 202 shaped strips, as well as a second panel 222 comprising a third shaped strip 203 and a fourth shaped strip 204, as shown in FIG. 11 and FIG. 12. One pair of shaped strips is thus formed on each side of the dividing cut pattern 238, and each pair is nested, as described above. Geometrically, the axes of symmetry of both of any nested pair of shaped strips are parallel. Shaped strips having parallel axes of symmetry have identical axial orientations.

The first shaped strip 201 and the third shaped strip 203, which have different axial orientations, are joined to form multi-directional shaped components 200. Likewise, the second shaped strip 202 and the fourth shaped strip 204, which have different axial orientations, are joined to form multi-directional shaped components 200. As shown in FIG. 11, the second web 240 is repositioned twice in the cross machine direction in this embodiment. The first repositioning places the second web 240 in position for the second shaped strip 202 to be joined and the second repositioning places the second web 240 in position for the third shaped strip 203 to be joined. Thus, in this embodiment, the third shaped strip 204 is joined at a third combining roll 314 when the second web 240 is aligned on a second repositioned centerline 244. Also, the first shaped strip 201 and second shaped strip 202 remain on the first panel 220 centerline 250 and the third shaped strip 203 and a fourth shaped strip 204 remain on the second panel 222 centerline 252 until each is joined to the second web 240.

In an exemplary alternative embodiment for forming multi-directional shaped components 200, the first shaped strip 201 and second shaped strip 202 may be cut as shown in FIG. 12, the first shaped strip 201 may be joined to the second web 240, the cross machine direction orientation of the second web 240 may be reversed as described above, and the second shaped strip 202 may then be joined to the reversed first shaped strip 201. Since the axial orientation of the first shaped strip 201 is altered by the reversal of its cross machine direction orientation, the axial orientations of the joined first shaped strip 201 and second shaped strip 202 differ.

As another example, the first web 140 may be cut into three shaped strips, and the composite web 400 may be formed as shown in FIG. 13. In this embodiment, as shown in FIG. 14, the first shaping cut pattern 234 and the second shaping cut pattern 236 form second shaped strip 202 and third shaped strip 203 along the longitudinal edges 144 of the first web 140 and first shaped strip 201 between the second shaped strip 202 and third shaped strip 203. When cut, the first shaped strip 201 has opposed projecting portions 218 which alternate with, and are nested with, the projecting portions 218 of the second shaped strip 202 and third shaped strip 203. In particular, the first shaping cut pattern 234 and the second shaping cut pattern 236 are substantially identical. Also, the first shaping cut pattern 234 and the second shaping cut pattern 236 are positioned substantially symmetrically relative to the centerline 142 of the first web 240, such that the width of each of the second shaped strip 202 and third shaped strip 203 is substantially half the width of the first shaped strip 201. In this embodiment, as in the four strip embodiment described above, the second web 240 is repositioned twice in the cross machine direction, first to a repositioned centerline 243 and then by a second repositioning distance 262 to a second repositioned centerline 244. The first shaped strip 201 remains on the first web centerline 142, the second shaped strip remains on the second shaped strip 202 centerline 254, and the third shaped strip 203 remains on the third shaped strip 203 centerline 255 until each is joined to the second web 240. In the resultant composite web 400, the projecting portions 218 of the second shaped strip 202 and third shaped strip 203 are superposed on the projecting portions 218 of the first shaped strip 201 to form a multilayer shaped strip whose shape is defined by the contour of the first shaped strip 201.

Figure 15:
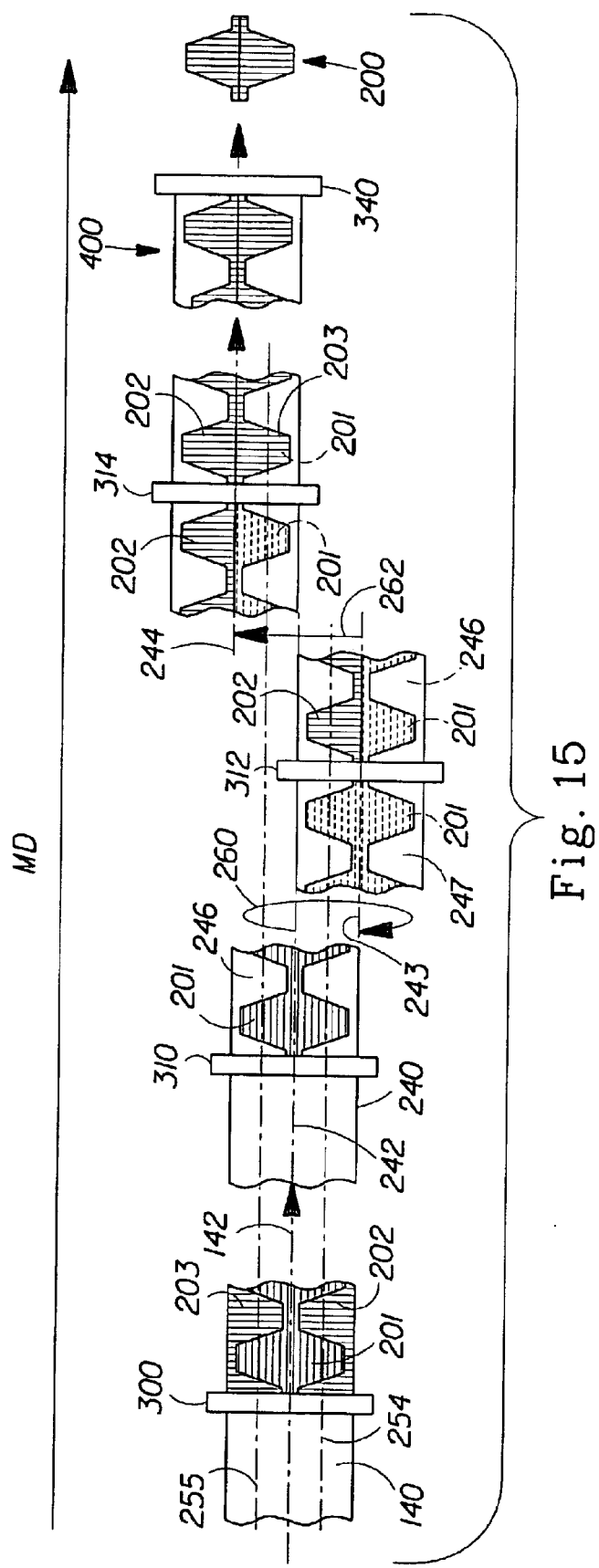
FIG. 15 is a schematic plan view of sequential portions of another alternative exemplary embodiment of the process of the present invention.

Alternatively, as shown in FIG. 15, the second web 240 may be reoriented to place it in position for the second shaped strip 202 and third shaped strip 203 to be joined on the opposing second surface 247 of the second web 240. In this alternative embodiment, by phasing the shaped strips and aligning the shaped strips in the cross machine direction, a single shaped strip having a shape defined by the contour of the first shaped strip 201 may thus be formed. This single shaped strip has a layer of the first web 140 material on each of the opposing first surface 246 and second surface 247 of the second web 240. In either embodiment of FIG. 13 or FIG. 15, the multi-layer shaped strip formed from the three original shaped strips may be cut in only the cross machine direction to form shaped components 200 having opposed projecting portions 218 or may be cut in more than one direction to form shaped components 200 having any desired shapes.

In addition, the process of the present invention may be used to make more than one composite web 400 comprising shaped strips derived from a single first web 140. For example, the first shaped strip 201 and fourth shaped strip 204 may be joined to the second web 240, while the second shaped strip 202 and the third shaped strip 203 may be joined to a fifth web. The net result may thus be two composite webs 400, each comprising bi-directional side panels.

After the formation of the composite web 400 comprising the shaped strips, the shaped components 200 are cut from the composite web 400. The pattern of this separating cut defines the edges of the shaped components 200. Each separate shaped component 200 preferably includes at least a portion of one of the projecting portions 218 of at least one of the shaped strips. The separating cut may be made by any of the means described above. For example, a separating die cutter 340 may be used to cut the shaped components 200 from the composite web 400.

After separation, the shaped components 200 may be positioned adjacent an absorbent article web, such as a diaper web. The shaped components 200 may be joined to any part of the diaper 20 in a position and an orientation suitable for their intended function.

Embodiments are also envisioned in which additional components may be joined on the shaped strips, on the shaped components 200, or on both, prior to or after the joining of the shaped components 200 to the diaper 20. For example, in any of the embodiments described above, fastening devices may be joined on the shaped strips and the shaped components 200 may thus form the side panels 30 on the diaper 20. Likewise, in some embodiments, the composite web 400 may be folded in order to form shaped components 200 having folded portions. For example, hook and loop fastening material may be joined on the first shaped strip 201, the composite web 400 may be folded to close the fastening system by engaging the hooks and loops, and the shaped components 200 may thus comprise closed hook and loop fastening devices.

While particular embodiments of the present invention have been illustrated and described, it would be obvious to those skilled in the art that various other changes and modifications could be made without departing from the spirit and scope of the invention. It is therefore intended to cover in the following claims all such changes and modifications that are within the scope of this invention.

What is claimed is:

1. A method for manufacturing shaped components from web materials, the method comprising the steps of:

provising a first web of material in a machine direction, the first web having longitudinal edge portions;

making at least a first shaping cut to sever the first web into at least a first shaped strip and a second shaped strip, the first shaping cut having a pattern extending in the machine direction and alternately extending in a cross machine direction to alternate distal points located between the longitudinal edge portions of the first web, the first shaped strip and the second shaped strip having alternating nested projecting portions defined by the first shaping cut;

separating the first shaped strip and the second shaped strip;

providing a second web of material in the machine direction;

joining at least the first shaped strip to the second web;

repositioning the second web in the cross machine direction such that the first shaped strip is in a predetermined position relative to the second shaped strip;

joining at least the second shaped strip to the second web; and making at least one separating cut to separate the shaped components, the separating cut having a pattern defining edges of the shaped components, each of the shaped components comprising at least a portion of one of the projecting portions of one of the shaped strips, wherein each of the first shaped strip and the second shaped strip moves in a direction parrallel to a centerline of the first web without movement in the cross machine direction until being joined to the second web.

2. The method of claim 1 further comprising the steps of:
providing a third web of material in the machine direction; and joining the third web to the second web so as to sandwich the first shaped strip and second shaped strip between the third web and the second web.

3. The method of claim 1 further comprising the step of reorienting the second web such that both the first shaped strip and the second shaped strip are joined to a first surface of the second web with the projecting portions of the first shaped strip projecting in a same direction as the projecting portions of the second shaped strip.

4. The method of claim 1 further comprising the step of reorienting the second web such that the first shaped strip is joined to a first surface of the second web and the second shaped strip is joined to a second surface of the second web.

5. The method of claim 1 wherein at least a portion of the second shaped strip is superposed relative to the first shaped strip.

6. The method of claim 1 further comprising the step of repositioning the second web in the cross machine direction after joining the second shaped strip to the second web.

7. The method of claim 1 further comprising the steps of:
making a second shaping cut to sever the first web into a third shaped strip, the second shaping cut having a pattern extending in the machine direction and alternately extending in the cross machine direction to alternate distal points located between the longitudinal edge portions of the first web, such that the first shaped strip is formed between the second shaped strip and the third shaped strip, the first shaped strip and the third shaped strip having alternating nested projecting portions defined by the second shaping cut;

separating the third shaped strip;

repositioning the second web in the cross machine direction such that the first shaped strip is in a predetermined position relative to the third shaped strip; and joining the third shaped strip to the second web.

8. The method of claim 7 wherein the second shaping cut has a pattern substantially identical to the first shaping cut pattern, the first shaping cut pattern and second shaping cut pattern being positioned substantially symmetrically relative to a centerline of the first web, such that a width of each of the second shaped strip and third shaped strip is substantially half a width of the first shaped strip.

9. The method of claim 1 wherein the first shaped strip and the second shaped strip have a common machine direction orientation.

10. The method of claim 1 wherein the repositioning of the second web in the cross machine direction occurs while the second web is continuously moving in the machine direction at a substantially uniform linear velocity.

11. The method of claim 1 further comprising the step of phasing the second shaped strip in the machine direction such that the second shaped strip is joined to the second web in a predetermined machine direction phase relationship relative to the first shaped strip.

12. The method of claim 1 wherein the first web comprises an elastomeric material.

13. The method of claim 12 wherein the first web comprises a laminate comprising the elastomeric material and a non-woven material.

14. A method for manufacturing multi-directional shaped components from web materials, the method comprising the steps of:

providing a first web of material in a machine direction, the first web having longitudinal edge portions;

making at least a first shaping cut to sever the first web into at least a first shaped strip and a second shaped strip, the first shaping cut having a pattern extending in the machine direction and alternately extending in a cross machine direction to alternate distal points located between the longitudinal edge portions of the first web, the first shaped strip and the second shaped strip having alternating nested projecting portions defined by the first shaping cut, the first shaped strip having an axial orientation substantially identical to an axial orientation of the second shaped strip;

separating the first shaped strip and the second shaped strip;

providing a second web of material in the machine direction;

joining at least the first shaped strip to the second web;

reorienting the second web such that the axial orientation of the first shaped strip differs from the axial orientation of the second shaped strip;

repositioning the second web in the cross machine direction such that at least a portion of the second shaped strip is aligned to at least partially overlap a portion of the first shaped strip in the cross machine direction;

phasing the second web in the machine direction such at least a portion of the second shaped strip is aligned to at least partially overlap a portion of the first shaped strip in the machine direction;

joining at least a portion of the second shaped strip to a portion of the first shaped strip; and making at least one separating cut to separate the multi-directional shaped components, the separating cut having a pattern defining edges of the shaped components, each of the shaped components comprising at least a portion of the joined portions of the first shaped strip and the second shaped strip.

15. A method for manufacturing multi-directional shaped components from web materials, the method comprising the steps of:

providing a first web of material in a machine direction;

making at least one dividing cut in the machine direction to sever the first web into at least a first panel and a second panel having longitudinal edge portions;

making at least a first shaping cut through the first panel to sever the first panel into at least a first shaped strip and a second shaped strip, the first shaping cut having a pattern extending in the machine direction and alternately extending in a cross machine direction to alternate distal points located between the longitudinal edge portions of the first panel, the first shaped strip and the second shaped strip having alternating nested projecting portions defined by the first shaping cut, the first shaped strip and the second shaped strip having an axial orientation;

making at least a second shaping cut through the second panel to sever the second panel into at least a third shaped strip and a fourth shaped strip, the second shaping cut having a pattern extending in the machine direction and alternately extending in a cross machine direction to alternate distal points located between the longitudinal edge portions of the second panel, the third shaped strip and the fourth shaped strip having alternating nested projecting portions defined by the second shaping cut, the third shaped strip and the fourth shaped strip having an axial orientation differing from the axial orientation of the first shaped strip and the second shaped strip;

separating at least the first shaped strip and at least one of the third shaped strip or the fourth shaped strip;

providing a second web of material in the machine direction;

joining at least the first shaped strip to the second web;

repositioning the second web in the cross machine direction such that at least a portion of the one of the third shaped strip or the fourth shaped strip is aligned to at least partially overlap a portion of the first shaped strip in the cross machine direction;

phasing the second web in the machine direction such at least a portion of the one of the third shaped strip or the fourth shaped strip is aligned to at least partially overlap a portion of the first shaped strip in the machine direction;

joining at least a portion of the one of the third shaped strip or the fourth shaped strip to a portion of the first shaped strip; and making at least one separating cut to separate the multi-directional shaped components, the separating cut having a pattern defining edges of the shaped components, each of the shaped components comprising at least a portion of the joined portions of the first shaped strip and the one of the third shaped strip or the fourth shaped strip.

16. The method of claim 15 further comprising the steps of:

providing at least one absorbent article web of material in the machine direction;

positioning at least one of the multi-directional shaped components in a predetermined position adjacent the absorbent article web; and joining the multi-directional shaped component to the absorbent article web.

17. The method of claim 15 further comprising the steps of:

separating at least the second shaped strip and an other of the third shaped strip or the fourth shaped strip;

joining at least the second shaped strip or the other of the third shaped strip or the fourth shaped strip to the second web;

repositioning the second web in the cross machine direction such that at least a portion of the other of the third shaped strip or the fourth shaped strip is aligned to at least partially overlap a portion of the second shaped strip in the cross machine direction;

phasing the second web in the machine direction such at least a portion of the other of the third shaped strip or the fourth shaped strip is aligned to at least partially overlap a portion of the second shaped strip in the machine direction; and joining at least a portion of the other of the third shaped strip or the fourth shaped strip to a portion of the second shaped strip.

18. The method of claim 15 wherein the multi-directional shaped components are elastically extensible side panels.

* * * * *

UNITED STATES PATENT AND TRADEMARK OFFICE
CERTIFICATE OF CORRECTION

PATENT NO.      : 6,743,324 B2
DATED           : June 1, 2004
INVENTOR(S)     : Mark Mason Hargett et al.

It is certified that error appears in the above-identified patent and that said Letters Patent is hereby corrected as shown below:

Column 15,
Line 17, delete "parrallel" and insert therefor -- parallel --.

Signed and Sealed this

Sixteenth Day of November, 2004

JON W. DUDAS
*Director of the United States Patent and Trademark Office*